(12) United States Patent
Sørensen et al.

(10) Patent No.: US 12,127,731 B2
(45) Date of Patent: Oct. 29, 2024

(54) HOUSING FOR THE TIP OF A DISPOSABLE INSERTION ENDOSCOPE

(71) Applicant: AMBU A/S, Ballerup (DK)

(72) Inventors: Morten Sørensen, Ballerup (DK); Jan Guldberg Hansen, Greve (DK)

(73) Assignee: AMBU A/S, Ballerup (DK)

( * ) Notice: Subject to any disclaimer, the term of this patent is extended or adjusted under 35 U.S.C. 154(b) by 433 days.

(21) Appl. No.: 17/600,479

(22) PCT Filed: Mar. 30, 2020

(86) PCT No.: PCT/EP2020/058932
§ 371 (c)(1),
(2) Date: Sep. 30, 2021

(87) PCT Pub. No.: WO2020/201205
PCT Pub. Date: Oct. 8, 2020

(65) Prior Publication Data
US 2022/0175224 A1    Jun. 9, 2022

(30) Foreign Application Priority Data

Apr. 2, 2019  (EP) .................... 19166789

(51) Int. Cl.
*G02B 1/18*    (2015.01)
*A61B 1/00*    (2006.01)
(Continued)

(52) U.S. Cl.
CPC ...... *A61B 1/00096* (2013.01); *A61B 1/00103* (2013.01); *A61B 1/0011* (2013.01);
(Continued)

(58) Field of Classification Search
CPC ............ A61B 1/00096; A61B 1/00103; A61B 1/0011; A61B 1/05; A61B 1/00142;
(Continued)

(56) References Cited

U.S. PATENT DOCUMENTS 5,193,525 A   3/1993  Silverstein et al.
8,029,438 B2  10/2011 Hagihara et al.
(Continued)

FOREIGN PATENT DOCUMENTS

EP    3539449 A1    9/2019
WO    2010/066790 A1    6/2010
(Continued)

OTHER PUBLICATIONS

Optical coating, Wikipedia, retrieved from "https://en.wikipedia.org/w/index.php?title=Optical_coating&oldid=1150837908".
(Continued)

*Primary Examiner* — Anh Tuan T Nguyen
*Assistant Examiner* — Shankar Raj Ghimire
(74) *Attorney, Agent, or Firm* — Faegre Drinker Biddle & Reath LLP

(57) ABSTRACT

A housing (1) for the tip of a disposable insertion endoscope includes a circumferential side wall (2) having a first end and a second end, and a front wall (3) arranged at the first end to provide an internal compartment (4) in the housing (1), the front wall (3) including at least one transparent part made of a polymer material and adapted to protect a camera (10) arranged in the housing behind the at least one transparent part and a front surface (15) having at least one area provided with a nano-structure.

12 Claims, 5 Drawing Sheets

Figure 1:
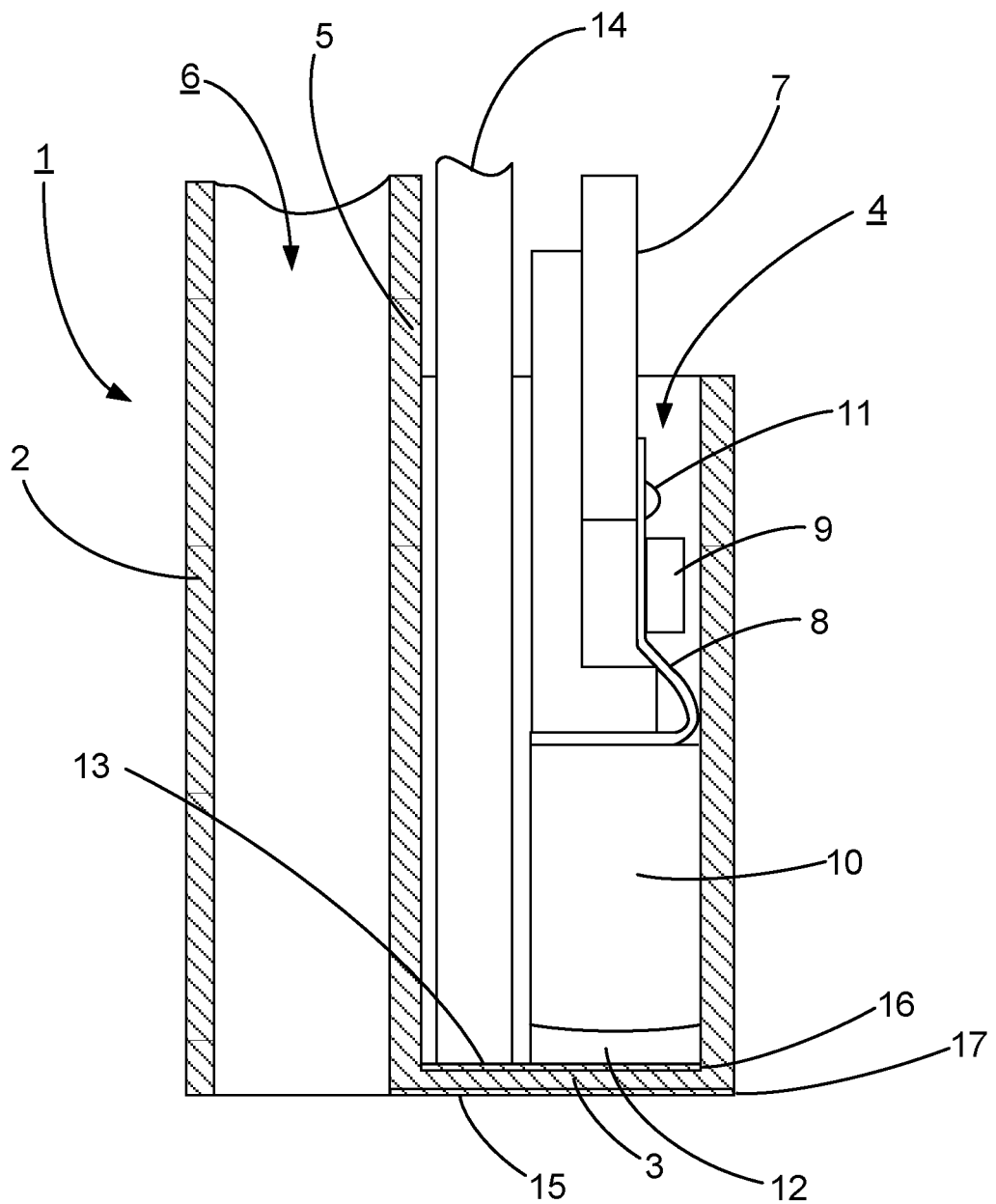

(51) Int. Cl.
*A61B 1/05* (2006.01)
*B82Y 30/00* (2011.01)
*G02B 1/118* (2015.01)
*G02B 27/00* (2006.01)

(52) U.S. Cl.
CPC .............. *A61B 1/05* (2013.01); *G02B 1/118* (2013.01); *G02B 1/18* (2015.01); *G02B 27/0006* (2013.01); *B82Y 30/00* (2013.01); *G02B 2207/101* (2013.01)

(58) Field of Classification Search
CPC ...... G02B 1/118; G02B 1/18; G02B 27/0006; G02B 2207/101; G02B 23/2423; B82Y 30/00
See application file for complete search history.

(56) References Cited

U.S. PATENT DOCUMENTS

| | | | |
|---|---|---|---|
| 8,381,728 B2 | 2/2013 | Rao et al. | |
| 10,182,707 B2 | 1/2019 | Kirma et al. | |
| 11,241,150 B2* | 2/2022 | Liu | A61B 1/0684 |
| 11,291,352 B2 | 4/2022 | Vilhelmsen et al. | |
| 2001/0056224 A1* | 12/2001 | Renner | A61B 1/00075 600/139 |
| 2005/0113936 A1* | 5/2005 | Brustad | A61L 31/082 623/1.46 |
| 2005/0136217 A1 | 6/2005 | Barthlott et al. | |
| 2008/0078386 A1 | 4/2008 | Feldhahn et al. | |
| 2008/0228035 A1 | 9/2008 | Hagihara et al. | |
| 2009/0180188 A1* | 7/2009 | Bach | G02B 1/118 359/601 |
| 2011/0270221 A1 | 11/2011 | Ross | |
| 2013/0157729 A1* | 6/2013 | Tabe | H04W 52/0245 977/932 |
| 2013/0175720 A1 | 7/2013 | Otsuka et al. | |
| 2013/0266761 A1 | 10/2013 | Ho et al. | |
| 2014/0147627 A1* | 5/2014 | Aizenberg | F15D 1/02 428/141 |
| 2014/0182587 A1 | 7/2014 | Dunne et al. | |
| 2014/0200466 A1 | 7/2014 | Sereno et al. | |
| 2014/0276407 A1 | 9/2014 | DeVries et al. | |
| 2014/0318657 A1 | 10/2014 | Bixler et al. | |
| 2015/0251201 A1 | 9/2015 | Hradetzky et al. | |
| 2015/0289751 A1* | 10/2015 | Frerck | A61B 1/127 264/293 |
| 2015/0306813 A1 | 10/2015 | Roehrig et al. | |
| 2016/0161823 A1* | 6/2016 | Kim | G02F 1/134309 349/15 |
| 2016/0229095 A1 | 8/2016 | Mori et al. | |
| 2016/0287058 A1 | 10/2016 | Ye et al. | |
| 2016/0370506 A1 | 12/2016 | David et al. | |
| 2017/0095242 A1 | 4/2017 | Milbocker et al. | |
| 2017/0146453 A1 | 5/2017 | Giles et al. | |
| 2019/0016084 A1 | 1/2019 | Hayashi et al. | |
| 2019/0136070 A1* | 5/2019 | Aizenberg | A61B 1/00071 |
| 2019/0282070 A1 | 9/2019 | Vilhelmsen et al. | |
| 2020/0064520 A1* | 2/2020 | Xiao | B32B 9/007 |
| 2020/0117022 A1* | 4/2020 | Gao | B29D 11/00788 |
| 2020/0174371 A1* | 6/2020 | Duan | B05D 1/02 |
| 2020/0333593 A1* | 10/2020 | Bard | C03B 27/012 |
| 2021/0093175 A1* | 4/2021 | Sørensen | A61B 1/00103 |
| 2022/0175224 A1* | 6/2022 | Sørensen | G02B 27/0006 |
| 2022/0240766 A1* | 8/2022 | Chang | A61B 1/00096 |
| 2022/0240980 A1* | 8/2022 | Chang | A61B 1/00096 |

FOREIGN PATENT DOCUMENTS

| | | | |
|---|---|---|---|
| WO | 2010105870 A1 | 9/2010 | |
| WO | WO-2014088191 A1 * | 6/2014 | .............. B05D 5/08 |
| WO | 2014/106511 A1 | 7/2014 | |
| WO | WO2017/189855 | 11/2017 | |

OTHER PUBLICATIONS

Anti Glare Film, Screen Solutions International, "https://www.ssiscreens.com/wp-content/uploades/anti-glare-film-1.jpg".

Christiansen, A., et al., "Injection moulding antireflective nanostructures", DTU Library 2013.

Extended European Search Report issued in European application EP 19166789.8, dated Sep. 10, 2019, 7 pages.

International Search Report and Written Opinion issued in PCT/EP2020/058932, mailed May 11, 2020, 8 pages.

* cited by examiner

HOUSING FOR THE TIP OF A DISPOSABLE INSERTION ENDOSCOPE

CROSS-REFERENCE TO RELATED APPLICATIONS

This application is a National Stage entry under 35 U.S.C. § 371 of International Application No. PCT/EP2020/058932, filed Mar. 30, 2020, which claims the benefit of and priority from European Application No. 19166789.8, filed Apr. 2, 2019; said applications are incorporated by reference herein in their entirety.

The present invention relates to endoscopes, in particular disposable insertion endoscopes, and more specifically but not exclusively to a housing of an insertion endoscope.

Endoscopes which in this context comprises endotracheal tubes provided with a camera as well as laryngoscopes provided with a camera, are well known devices for visually inspecting inaccessible places such as human body cavities. Endoscopes include insertion endoscopes and capsule endoscopes. Capsule endoscopes are capsules which are normally administered orally and pass through the digestive system. Insertion endoscopes on the other hand are inserted into the body via suitable openings, be it natural or purpose-provided. Insertion endoscopes typically comprise an elongated insertion tube with a handle at the proximal end as seen from the operator and visual inspections means, such as a built-in camera, at the distal end of the elongated insertion tube. Electrical wiring for the camera and other electronics such as LED lighting accommodated in the tip part at the distal end run along the inside of the elongated insertion tube from the handle to the tip part. Instead of using cameras, endoscopes may also be fibre-optic, in which case the optical fibres run along inside of the elongated insertion tube to the tip part.

In order to be able to manoeuvre the endoscope inside the body cavity, the distal end of the endoscope may comprise a bending section with increased flexibility, e.g. a number of articulated segments of which the tip part forms the distal-most segment. This is typically done by tensioning or slacking pull wires also running along the inside of the elongated insertion tube from the tip part through the remainder of articulated segments to a control mechanism of the handle. Furthermore, a working channel may run along the inside of the insertion tube from the handle to the tip part, e.g. allowing liquid to be removed from the body cavity or allowing the insertion of surgical instruments or the like into the body cavity.

Modern endoscopes are typically equipped with a least one camera or similar image capturing device at the distal tip of the endoscope. Provided that sufficient light is present, this allows the operator to see where the endoscope is steered and to set the target of interest once the tip has been advanced thereto. This therefore normally requires illumination of the area in front of the distal tip of the endoscope, in particular the field of vision of the camera(s). One known way of achieving such illumination is to provide the above mentioned LED lighting using one or more Light Emitting Diodes (LEDs) in the tip of the endoscope, as e.g. mentioned in WO2014/106511 disclosing a disposable endoscope.

When, as in the present invention, the insertion tube of the endoscope is intended to be inserted into a human body cavity, the insertion tube needs to be sealed in a watertight manner. This is in particular the case for the distal tip part because it accommodates the camera, LED(s) and other delicate electronics, prone to malfunction or destruction if exposed to humidity.

One known way of sealing the tip part of an endoscope is disclosed in WO2010/066790. In this document a transparent monolithic housing is formed around the electronics and working channel by placing the electronics and the tube forming the working channel in a mould of transparent material, such as silicone. A transparent UV curable resin is then injected from the bottom of the mould to avoid bubbles to form in the transparent resin. Because the resin rises slowly from the bottom, the air is slowly expelled from top of the mould, without any risk of air bubbles being trapped in the mould. The resin is then cured using UV irradiation through the transparent mould to form the monolithic housing. However, forming a monolithic housing in this way has some drawbacks. One is that it is a somewhat slow process. Another is that it can be difficult to position and maintain the components precisely in position during the injection of the resin. Thus, the camera or LEDs may in few cases be off-set sideways or a thin transparent layer may inadvertently be created in front of the camera and/or LEDs, thereby reducing the imaging qualities of the tip part. This will lead to the product being discarded in the quality control, thereby increasing overall cost of manufacturing.

Alternatively, a generally cup-shaped housing with an at least partially transparent bottom forming front wall at the distal end of the endoscope could be used. Partially transparent in this context is to be understood as transparent in some areas and opaque in others. In this case the transparent parts form a front window in front of the camera and light sources, such as LEDs, accommodated in the cup-shaped housing.

The transparent front window or the inadvertently created thin layer of transparent material may result in undesired stray light from the LEDs which through the transparent housing itself is reflected back from the front surface thereof because of the change in refractive index to the surroundings. This reflected light may impinge on the sensor of the camera and thereby disturb the captured images.

In this respect it is known from US2015/0289751 to chemically provide a nano-particle structure on a polymer surface in conjunction with a laparoscope.

The inventors have realized that in the context of disposable insertion endoscopes these problems may be overcome by the use of nano-structuring, even though the very fine and hence delicate nano-structuring is highly prone to damage, deterioration or destruction from external mechanical influence. This, however, turns out not to be a problem because the endoscope is to be disposed of after use with one patient, rather than having to go through a rather harsh cleaning and sterilisation procedure.

Thus, according to a first aspect of the present invention the problems is thus solved by providing a housing for the tip of a disposable insertion endoscope, said housing comprising a circumferential side wall having a first end and a second end, and a front wall arranged at the first end of said circumferential side wall, so as to provide an internal compartment in said housing, said front wall comprising at least one transparent part made of a polymer material and adapted to protect a camera arranged in said housing behind said at least one transparent part, said at least one transparent part comprising a first inner surface facing the internal compartment and a second surface opposite the first inner surface, wherein said second surface comprises at least one area provided with a nano-structure formed directly in said second surface.

Providing the nano-structure directly in the transparent polymer material furthermore obviates the risk of fragments of a separate coating detaching from the front surface, and thus the risk of potential exposure of the patient to such fragments.

According to a second aspect of the present invention, the problem is solved by a method for providing a housing according to the first aspect of the invention, said method comprising providing a mould cavity having a bottom and a circumferential wall, forming in said mould cavity a housing comprising a circumferential side wall having a first end and a second end, and a front wall arranged at the first end of said circumferential side wall, so as to provide an internal compartment in said housing, wherein at least a part of said front wall part is made from a transparent polymer material, where said at least one front wall part comprises a first inner surface facing the internal compartment and a second surface opposite the first inner surface, and providing a nano-structure directly in said transparent polymer material.

According to a third aspect of the invention, the problem is solved by a disposable insertion endoscope comprising a housing according to the first aspect of the invention.

Providing the nano-structure directly in the transparent polymer material furthermore avoid the risk of fragments of a separate coating detaching from the front surface, and thus the risk of potential exposure of the patient to such fragments.

According to a first preferred embodiment of the first aspect of the invention, the nano-structure comprises features extending perpendicular to the second surface, said features comprising one or more features selected from the group comprising peaks, ridges, ribs, pits, valleys and trenches.

Such structures are relatively easy to provide during manufacture and may by suitable selection allowing for anti-reflection properties and/or for either hydrophile or hydrophobic properties. The hydrophobic properties allow self-cleaning of the surface, and will also facilitate more efficient cleaning of a front window of the endoscope when the endoscope is provided with a cleaning nozzle for removing dirt or mucous by a water or air flow.

According to another preferred embodiment of the first aspect of the invention, the features comprise peaks with a spacing from one peak to the closest adjacent peak of less than 380 nm, preferably in the range of 200 nm to 300 nm. Spacings in these ranges are below visible wavelengths of light and will not, except for the desired anti reflection properties, interfere with the light transmission properties as such.

According to yet another preferred embodiment of the first aspect of the invention, the features comprise peaks with a spacing from one peak to the closest adjacent peak of less than 30 µm, preferably in the range of 50 nm to 30 µm. Peaks with spacings in these ranges will provide the front with hydrophobic properties, allowing the tip of the endoscope to be self-cleaning, e.g. under its own motion, be it with or without the presence of liquids in a body cavity. Cleaning by water from a nozzle will also be easier. Such water nozzles for cleaning a front window are often applied in gastroscopes or colonoscopes.

According to a further preferred embodiment of the first aspect of the invention, the nano-structure in said at least one area is provided according to a predetermined pattern. Predetermined patterns in the at least one area have been found to exhibit better properties, in particular in terms of anti-reflection over random nano-structures, i.e. random distribution of the features.

According, to yet another preferred embodiment of the first aspect of the invention, the features, the spacing, the pattern and/or combinations thereof are adapted to provide both hydrophobic and anti-reflective properties. Dual purpose can thus be achieved in one and the same housing, and in one single manufacturing stage.

According to a first preferred embodiment of the method of the second aspect of the invention, the nano-structure is provided directly in said transparent polymer material in a stamping process. Stamping of the nano-structure into the polymer requires less investment in the manufacturing process than the provision of a complementary nano-structure in a moulding cavity. This thus renders itself for small series, or variations in the patterning of the front wall of the tip housings of otherwise identical endoscopes.

According to a further preferred embodiment of the second aspect of the invention, said moulding cavity comprises a complementary nano-structure, so as to provide said nano-structure directly in said transparent polymer material in the moulding process. This allows the nano-structure to be provided directly during the moulding process, thus obviating an additional handling step for providing the nano-structure.

Figure 2:
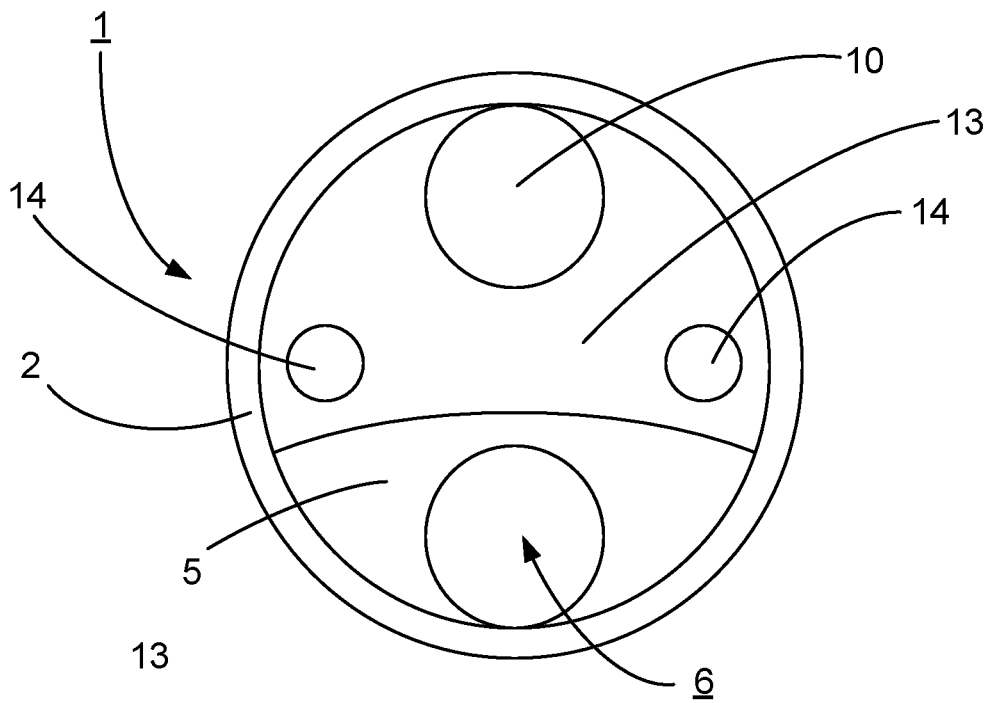
Figure 3:
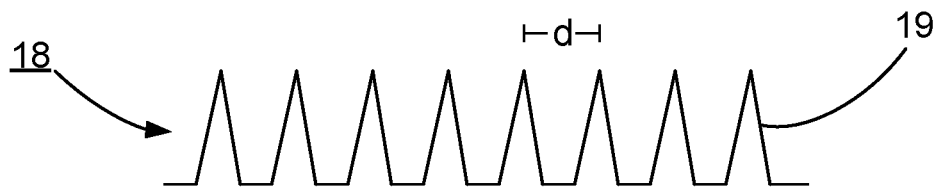
Figure 6:
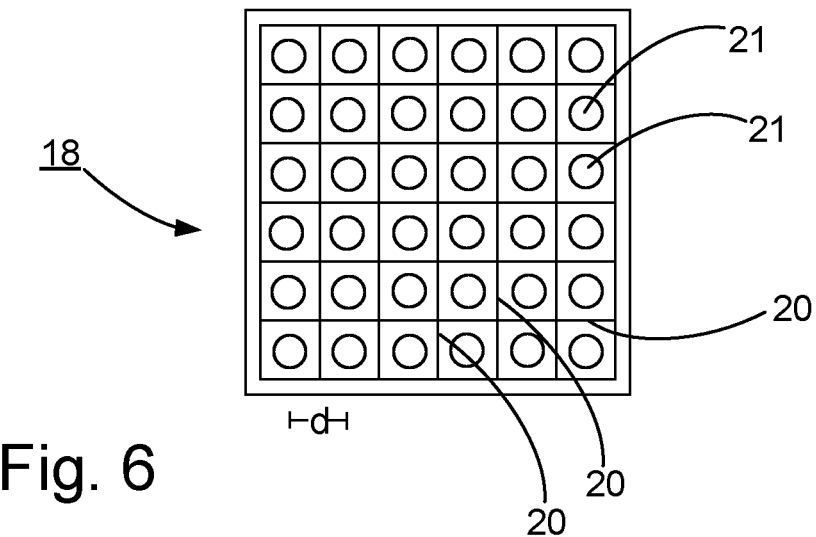
Figure 7:
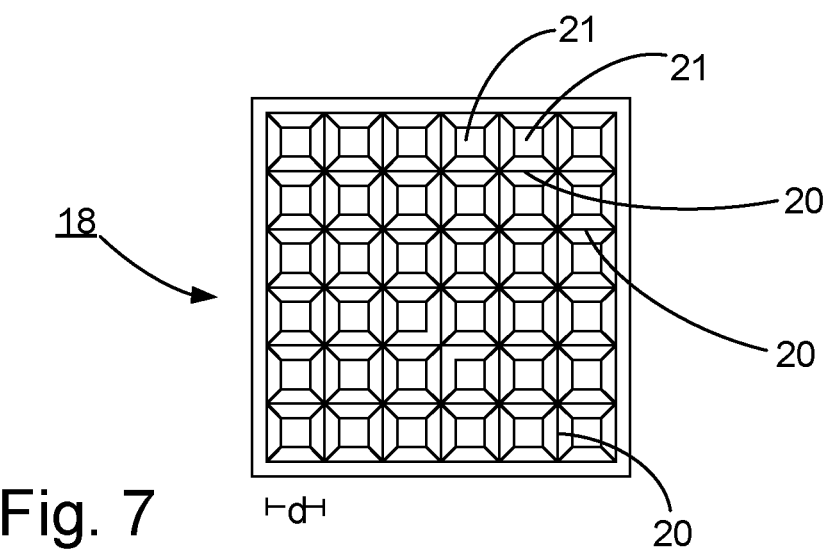
Figure 8:
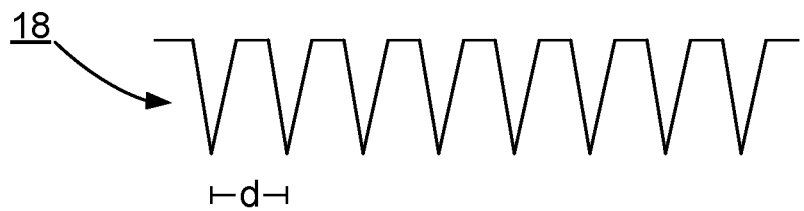
Figure 9:
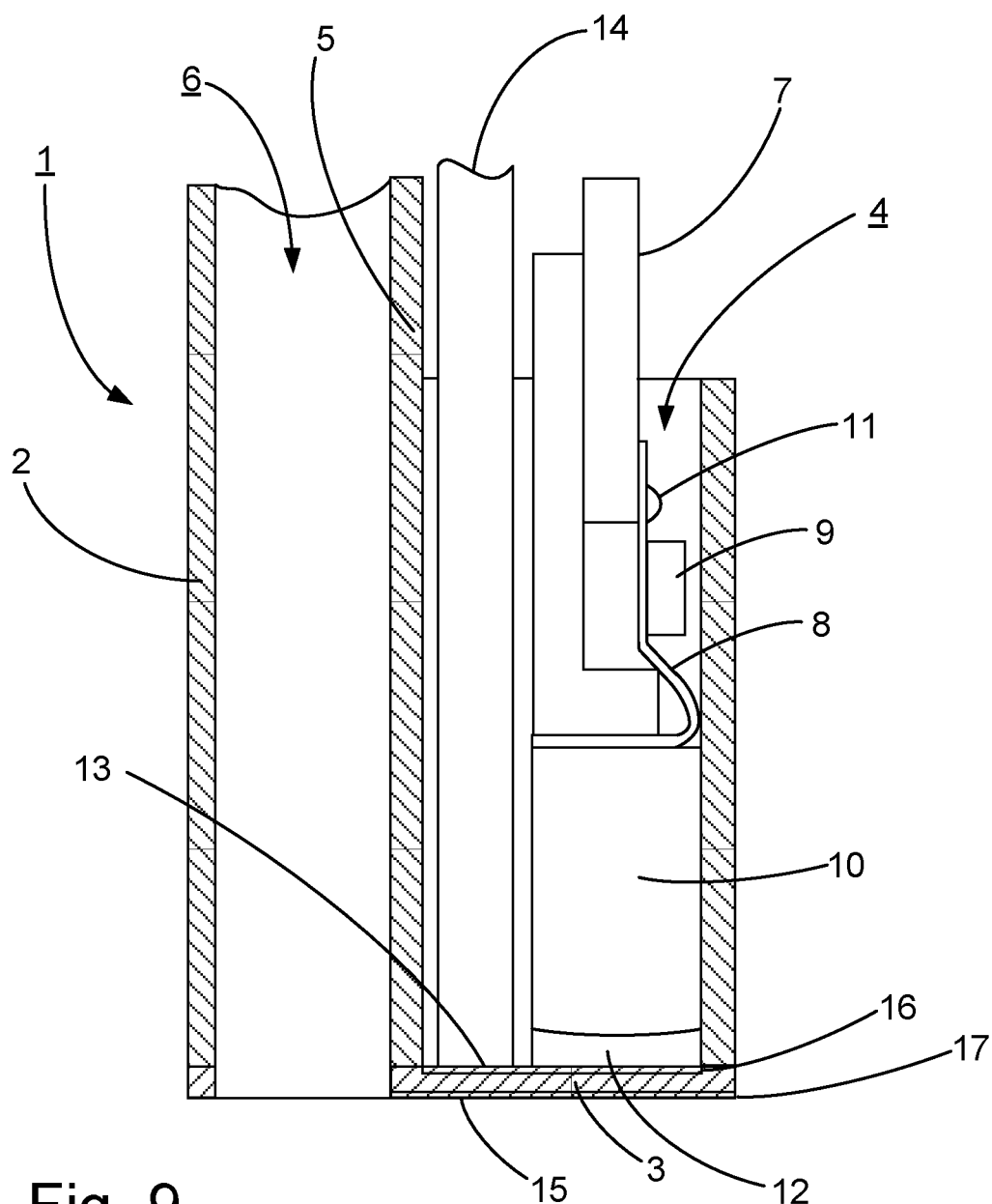
Figure 10:
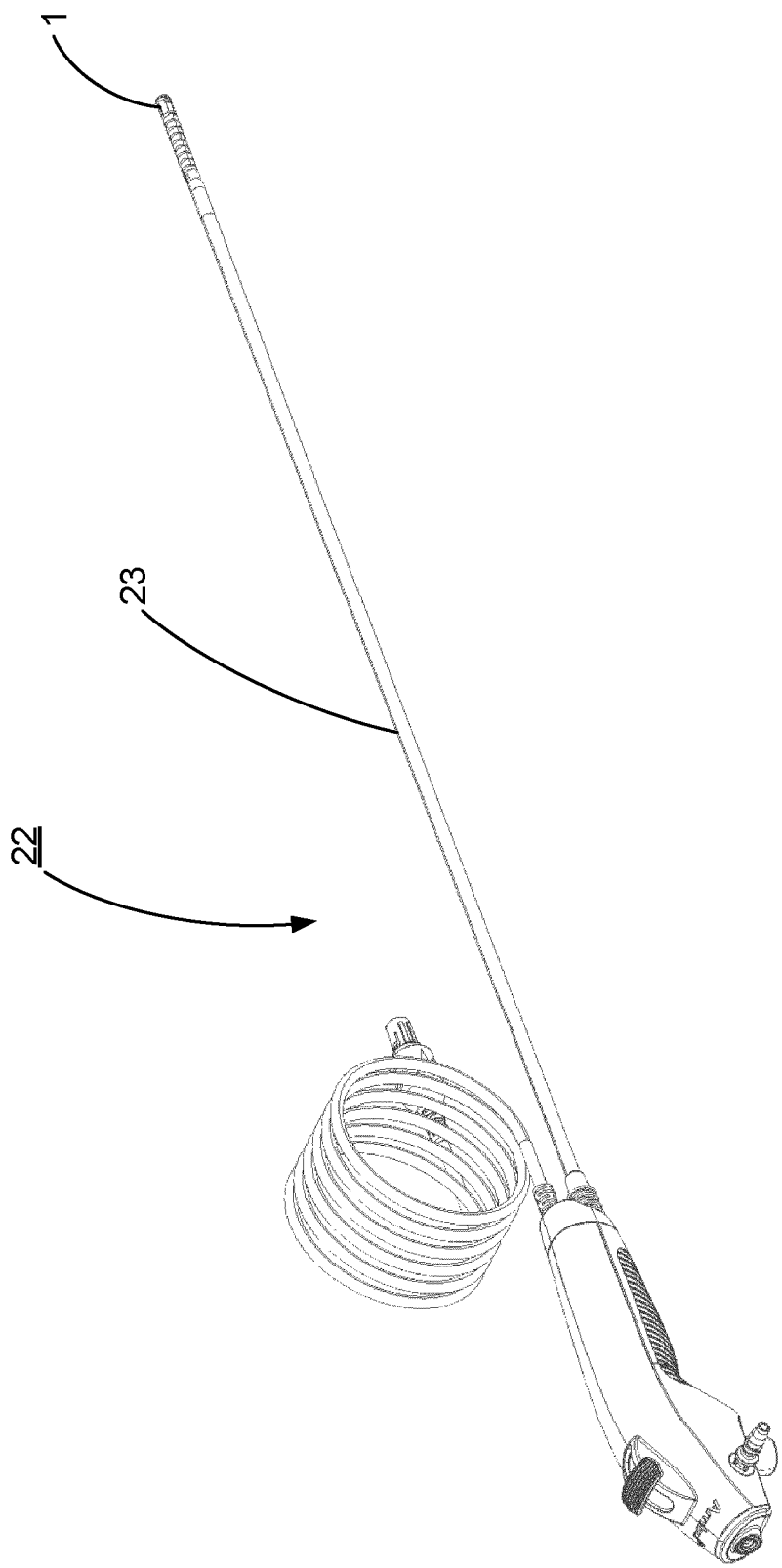

The invention will now be described in greater detail based on non-limiting exemplary embodiments and the drawings on which:

FIG. 1 shows a schematic cross-section of a first embodiment of a housing for the tip of a disposable endoscope, FIG. 2 shows a schematic view of the front of the housing of FIG. 1, FIG. 3 schematically shows a side view of an exemplary nano-structure applicable to the invention, FIGS. 4 to 7 schematically show plan views of exemplary nano-structures applicable to the invention, FIG. 8 schematically shows a side view of an alternative nano-structure applicable to the invention, FIG. 9 shows a schematic cross-section of a second embodiment of a housing for the tip of a disposable endoscope, similar to that of FIG. 1 but made of more than one material, and FIG. 10 shows a disposable endoscope in which the tip and the nanostructures of FIGS. 1 to 9 may be implemented.

Turning first to FIG. 10, a disposable endoscope 22 of the insertion type is shown. At the distal end, the disposable endoscope 22 comprises a housing 1 for the tip as shown in FIG. 1. As can be seen in FIG. 1, the housing 1 has a circumferential, preferably cylindrical outer side wall 2. The thickness of the wall is preferably between 0.1 and 0.25 mm more preferred between 0.1 and 0.2 mm to provide as much space in an inner compartment 4 without increasing the outer diameter of the tip of the insertion endoscope 22 unnecessarily. The housing 1 furthermore has a front wall 3 at a first end of the circumferential side wall 2 to provide the above mentioned inner compartment 4. The second end of the circumferential wall 2 is open for access to the compartment and insertion of components therein. The housing 1 in the embodiment shown furthermore has an inner partition 5, in order to provide a working channel 6 through the tip of the disposable endoscope 22, separate from the compartment 4. Whether the housing is provided with a working channel or not is, however, not as such relevant for the present invention. The front wall 3 is preferably made from a transparent polymer material, but may optionally comprise areas of opaque material (not shown). The front wall comprises a first or inner surface 13 facing inner compartment 4, and an outer front surface 15 or second surface forming the front of the tip of the disposable insertion endoscope 22. The rest of the housing may be made from the same transparent material, or it may be made from other polymer materials with other desirable properties, such as compatibility with adhesives, opaqueness, resiliency etc. as will be described further below in conjunction with FIG. 8. In that case the housing 1 is preferably made integrally as a single item in a two-component injection moulding process, e.g. as in the embodiment illustrated in FIG. 8.

In the inner compartment 4 a camera assembly is accommodated. In the illustrated embodiment the camera assembly comprises a carrier 7, a flexible circuit board 8 with auxiliary electronic components 9 between a camera 10 and connection means 11, such as solder, for electrical wiring (not shown) to the outside of the endoscope 22. The camera assembly may incorporate a lens 12, be it as a separate item or as an integral part or the camera 10. The skilled person will understand that, conversely, the at least one transparent part forming the front wall 3 may constitute a part of the camera, in particular the front lens of the camera accommodated in the housing 1. The camera assembly including the carrier is adapted to be inserted into the housing 1 and abut the inside surface 13 of the front wall 3 in firm engagement in order to avoid air filled gaps that may increase the risk of light reflections into the camera.

In order to provide light for the camera to see with an illumination device is likewise provided in firm abutting engagement with the inside surface 13 of the front wall 3. In the illustrated embodiment the illumination device 14 is an optical fibre through which light if fed from a remote light source providing light in the visible spectrum i.e. wavelengths above 380 nm. However, LEDs abutting the inside surface of the front wall 3 and supplied through electrical wiring from a remote power source would also be an option. This light should also be in the visible spectrum above 380 nm wavelength.

As indicated above one of the problems solved by the present invention is the glare and reflections in the transparent material of the front wall 3. That is to say because of the differences in refractive indices between the transparent material of the front wall 3 and the media in front of and behind the inner surface 13 and the front surface 15, respectively, thereof, reflections will normally occur. That is to say light emitted from the distal end of the illumination device 14 at the inner surface 13 may be reflected back from the front surface 15 into the camera, without ever exiting in front of the tip of the endoscope 22 where it is intended and needed for illumination of objects of interest. If no measures are taken the reflection in such an interface, i.e. the front surface can be as high as 4%, depending of course on refractive indices of the media on either side of the interface. This is a particular problem in the tips of endoscopes, because the lateral distance between the illumination device 14 and the camera 10 is very small. In some disposable endoscopes, the diameter of the tip may be 5 mm or less or even 3 mm or less leaving only substantially less than 1 mm between the output aperture of the illumination device 14 and the input aperture of the camera 10. With a preferred thickness of 0.4 mm or more the front wall 3 for strength reasons, it does not take many internal reflections within the front wall 3 before stray light enter the camera 10, and it is therefore important to reduce the percentage of reflected light in each of these reflections.

To inter alia avoid this glare stemming from these reflections one or both of the inner surface 13 and the front surface 15, but preferably only the latter, have according to the invention been provided with one or more areas 16 and 17 having a nano-structure 18, as will be exemplified and explained with reference to FIGS. 3 to 7 below. Please note that for illustration purposes the thicknesses of these areas 16 and 17 are extremely exaggerated in the schematic illustrations of FIGS. 1 and 2. Such nano-structures may reduce the reflection to values in the range of 0.1% as compared to the above mentioned 4%. Thus after only one or two reflections, the glare seen by the camera will have almost vanished.

However, providing a nano-structure 18 on the outside surface may also provide the front surface with hydrophobic properties and introduce self-cleaning effects by liquids running off the surface under the motions of the tip. Also, hydrophobic properties will make active cleaning by flow of e.g. water from a nearby nozzle more efficient.

Turning now to FIG. 2 the housing is shown from the front surface 15 of the front wall 3, i.e. is seen from the distal end of the endoscope 22. The diameter of the tip corresponding to the front wall of FIG. 2 is preferably less than 5 mm more preferred less than 3 mm for good accessibility of the endoscope 22 to body cavities. Through the transparent front surface 15 the parts lying behind it, i.e. the circumferential wall 2, the partition 5, the working channel 6, the camera 10, and the illumination devices 14, can be seen. The nano-structure 18 is obviously not visible, as is also not the transparent front surface 15. The entire front surface 15 may be covered with one and the same nano-structure 18, or different areas may be provided with nano-structures 18, the nano-structure 18 of the different areas may differ in properties, e.g. being optimized for anti-glare or for hydrophobic properties.

Figure 4:
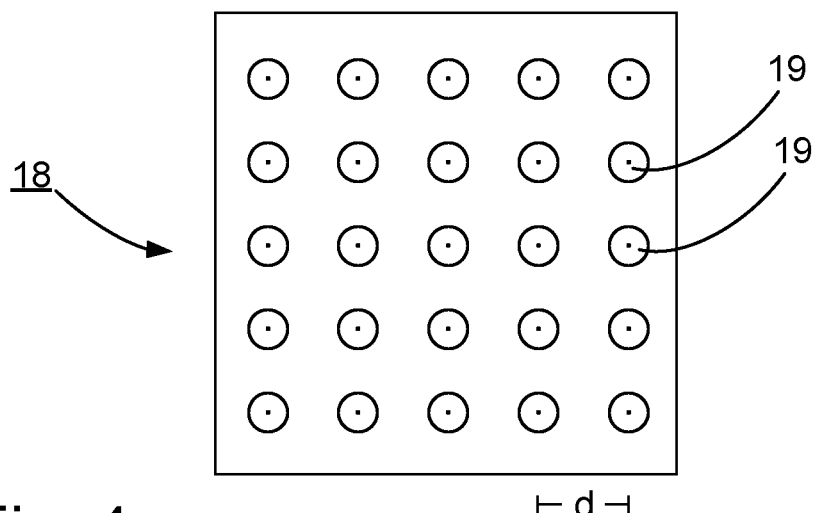
Figure 5:
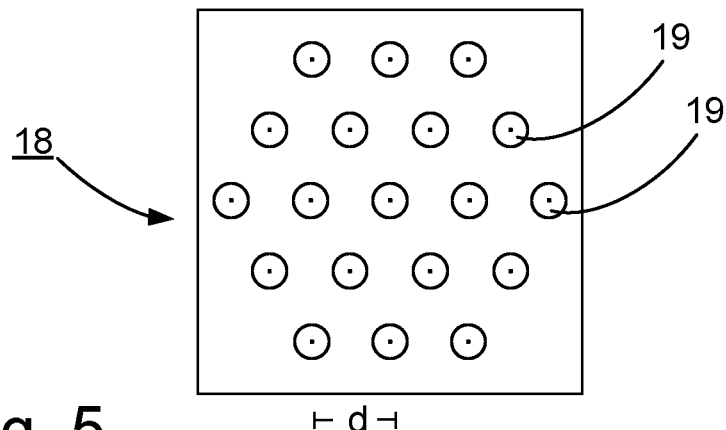

As can be seen in FIGS. 3 to 8 the nano-structure 18 comprises features 19, 20, 21 extending generally perpendicular from the overall plane of the surface, be it the first inner surface 13 or, as preferred, from the front surface 15, or even both. The surfaces are preferably smooth except for the features 19, 20, 21 and plane, the plane of the surface extending transversely to the optical axis of the camera 10 of the camera assembly and/or to the illumination device 14. The features of FIG. 3, as can be seen, are preferably identical elements such as peaks 19 in the shape of cones or pyramids arranged in predetermined patterns in one or two dimensions. In the simplest form the pattern consists in the peaks being equidistant in one predetermined direction, as shown schematically in FIG. 3. Of course, because an area has to be covered, the pattern will normally also be repetitive in a second dimension as illustrated in FIG. 4, where cones are arranged in a square grid manner, where a fourth order symmetry is provided. Another pattern with sixth order symmetry, i.e. a hexagonal pattern is illustrated in FIG. 5 but as the skilled person will realize there are numerous patterns where the features are repetitive and/or where neighbouring features are equidistant. This does not limit itself to cones 19 or pyramids, but includes ribs or ridges 20 separated by valleys if the ribs or ridges 20 are in parallel or concentric, or pits 21, if as illustrated in FIGS. 6 and 7, the ridges 20 cross each other. As illustrated in FIG. 8, the examples illustrated above may also in some embodiments be inverse, that is to say extending perpendicular into the front surface. In other words, where first embodiments have peaks, ridges, ribs, separated by pits, valleys and trenches, inverse will have pits, valleys and trenches separated by ridges, ribs or plateaus forming the outermost of the front surface 15. In some embodiments the features need not be pointed or have apexes, but could comprise plateaus separated by trenches.

Often, however, peaks in the shape of cones are preferred. These are preferably arranged in hexagonal patterns as illustrated in FIG. 5 where the spacing d from a given cone to all six neighbouring cones is the same.

The distance d will depend on the properties desired for the front surface 15. If only hydrophobic properties are desired of the spacing d from one peak to the closest adjacent peak should preferably be less than 30 μm, preferably in the range from 50 nm to 30 μm.

If instead, or additionally, anti-glare properties are desired, the spacing d between the features should be less than wavelengths of visible light in order not to disturb light transmission through the front surface 15 if the nanostructure 18 is present in the field of view of the camera 10. Thus, the spacing d between the features is preferably less than 380 nm, preferably in the range from 200 nm to 300 nm.

The height of the features will typically be approximately the same as the spacing d between them, or at least in the same order of magnitude, e.g. a height in the range of ½d to 2d, i.e. half to twice the spacing d.

Preferably, nano-structures 18 are only present on the transparent parts of the housing 1, i.e. the front 3. Only in the transparent parts is the need for anti-glare and self-cleaning imminent, and providing nano-structures 18 in other areas of the housing 1 is considered unnecessarily difficult. This is in particular the case when the housing is a two-component moulded tip, e.g. molded integrally from a transparent and a non-transparent material in one single moulding process, where it can be difficult to provide nano-structure 18 to both materials of a two-component molded part. This, however does not exclude that different types of nanostructures 18 are provided at the distal front of the tip. Thus, the above-mentioned nano-structures 18 with the spacing d less than 380 nm, e.g. in the range from 200 nm to 300 nm between the features 19, 20, 21, could be used in the area of the front surface 15 in front of the camera 10 and/or in front of the illumination device 14. The remainder of the front surface 15 could then be covered with nanostructures providing good self-cleaning properties, i.e. where the spacing d from one peak to the closest adjacent peak is less than 30 μm, preferably in the range from 50 nm to 30 μm in order to provide hydrophobic properties. A hydrophobic structure next to the camera window may reduce the risk of something sticking there and also blocking part of the image field of view.

It should be noted that under certain circumstances it is in fact possible to superpose two different nano-structures 18. That is to say if the spacing d, the features and/or the pattern characterizing the anti-glare properties and the spacing d, the features and/or the pattern characterizing the hydrophobic properties differ sufficient to not disturb each other they can be provided in the same area. If, as an example, the hexagonal structure of FIG. 5 is laid out with a spacing d of 30 μm between cones, there will be plenty of space between those cones 19 for other features, e.g. smaller cones 19 with a smaller spacing of e.g. 200 nm.

It is currently preferred to only provide nano-structure 18 on the external surfaces. That is to say, even if, as illustrated, nano-structures 18 may be provided in an area 16 on the inner surface 13, this is not necessarily desirable. Not only are they more difficult to provide, but experiments have indicated that in fact they do not provide the beneficial anti-glare desired. The self-cleaning properties are evidently not a matter of concern in areas that liquids and contaminants should not reach in a disposable insertion endoscope 22.

The nano-structure 18 is preferably provided directly in a moulding process, but may be provided later in a stamping process, e.g. by heating the polymer material to make it soft plastic again and stamping it with a suitably nano-structured stamp. In either case the nano-structure is ready to use and does not require any further treatment, such as additional anti-glare coatings or hydrophobic coatings.

As to the manufacturing process the housing 1 is preferably made by injection moulding of one or more suitable polymer material. That is to say the entire housing may be manufactured by injection moulding using a single transparent material injected into a single mould cavity with an external shape matching the desired exterior of the housing. That is to say, the housing 1 will comprise a circumferential wall and a bottom formed integrally as a single piece from one and the same material. For a generally cup-shaped housing 1, as illustrated in FIG. 1 where the circumferential wall is cylindrical the external shape of the mould cavity would be a cylindrical cavity with a generally flat bottom, save for the nano-structure and possibly the working channel passage. The working channel could of course also be provided by the counterpart of the mould cavity, or if necessary by suitable inserted cores.

To provide the nano-structure 18 the bottom of the mould cavity is preferably lined with an interchangeable prefabricated shim with engraved, etched or otherwise imprinted with a negative of the desired nano-structure. An example of a process for making such a shim, and a corresponding nano-structure, is disclosed in the document "Injection moulding of antireflective nanostructures", Christensen, A. B. et al, DTU Orbit, 2013, available from URL: <http://orbit.dtu.dk/files/97131108/AlexanderBC_MNE2013 poster.pdf>. In this document a master pattern corresponding to the desired nano-structure is etched in black silicon. A nickel shim is then provided by electroplating the black silicon. The nickel shim subsequently coated with an anti-stick coating. The coated nickel shim is placed in a mould and an item with an anti-reflective surface is then injection moulded from a black polymer. The suggestion is made that this may be useful for replacing anti-reflective coatings for camera objectives and other glass items. How this is to be done, and how to proceed from an opaque black polymer towards replacement of transparent lens coatings is not disclosed. A nano-structure for a stamp could be prepared as a shim in a similar manner.

The transparent material may be selected from various types of polymers, such as thermoplastic, thermosetting plastic, or silicone. The latter could be advantageous in that it can be injected as a low viscosity liquid, well able to enter into the fine details of the nano-structured shim before setting to form the nanostructure 18 directly in the material of the front wall 3. Silicone would have the further advantage of having also inherent hydrophobic properties. Other useful polymers would be PC, COC, COP, PMMA or ASA, and the skilled person will readily be able to identify further polymers having suitable properties in terms of e.g. biocompatibility, mechanical strength, brittleness, transparency, adhesiveness, etc.

In respect of allowing the polymer to enter into the fine details of the nano-structure of the mould it may be of advantage to apply vacuum to the mould in order to avoid air being trapped in the fine nano-structure and hindering the proper ingress of the polymer material.

Rather than making the housing 1 from one single material, it may also be made from two or more materials with different material properties, one of which obviously being transparency in order to form the front wall 3 or transparent front areas matching the locations of the camera 10 and the illumination device (or devices). The other material or materials may be optimised for other properties such as compatibility with adhesives, opaqueness, resiliency, etc. As can be seen from FIG. 8 an example of a preferred embodiment has a transparent front wall 3 made from a different material from the circumferential outer side wall 2. This material could be opaque, and preferably with a dark colour such as black in order to absorb stray light. It could also have good adhesive properties in order to secure a sealing outer sheath (omitted in FIG. 10 for illustration purposes) of the insertion tube 23 of the endoscope 22 to the housing 1 of the tip, or for adhering to a sealing material serving as a closure of the housing 1 to protect the electronic components.

The housing 1 according to FIG. 1 can be made in a two-component moulding process, where in a first stage the circumferential wall 2 is first moulded in a first mould cavity closed by a closure part. The moulded circumferential wall 2 is then moved on the closure part to a second mould cavity slightly larger than the first mould cavity in order to provide a mould cavity corresponding to the front wall 3. This second mould cavity in that case being lined with the shim carrying the complementary nano-structure. Then in a second moulding step the transparent polymer material of front wall 3 is injected and sets to form the front wall 3 with the nano-structure 18. In the second stage of the process a higher injection pressure may be used as compared to the first stage, in order to secure proper ingress of the material into the complementary nano-structure of the shim, thus forming the nano-structure directly in the material of the front wall 3.

It should be noted that the use of nickel shim is not the only way of providing the complementary nano-structure, it may be formed in other materials or even directly in the wall of the mould cavity in which the front wall 3 is moulded.

The invention claimed is:

1. An endoscope comprising:
    a camera; and
    a housing, said housing comprising:
        a circumferential side wall having a first end, a second end, and a front wall arranged at the first end of said circumferential side wall, the first end being distal of the second end, and the circumferential wall and the front wall providing an internal compartment in said housing,
        said front wall comprising at least one transparent part made of a polymer material and adapted to protect the camera, the camera being arranged in said internal compartment proximally of said at least one transparent part,
        said at least one transparent part comprising a first surface facing the internal compartment and a second surface opposite the first surface,
        wherein said second surface comprises at least one area having a nano-structure molded or stamped directly in said front wall,
        wherein the nano-structure in said at least one area comprises a predetermined pattern of features, the features comprising first features and second features,
        wherein a spacing between the first features is greater than a spacing between the second features, wherein the second features are disposed between adjacent ones of the first features, and
        wherein the first features are sized and structured to repel liquids and the second features are sized and structured to provide anti-reflective properties.

2. The endoscope of claim 1, wherein the first features comprise protrusions having peaks with the spacing from one peak to a closest adjacent peak of the first features being of less than 380 nm.

3. The endoscope of claim 1, wherein a remainder of the front wall surrounding the at least one area comprises a nano-structure comprising protrusions having peaks with a spacing from one peak to the closest adjacent peak in the range of 50 nm to 30 μm.

4. The endoscope of claim 1, wherein the spacing between the first features is in the range of 200 nm to 300 nm.

5. The endoscope of claim 2, wherein the second surface comprises a plane and the protrusions extend from and perpendicular to the plane of the second surface.

6. The endoscope of claim 2, wherein each of the features comprises a base, and wherein the protrusions comprise one or more of pyramids, cones, ridges, or ribs.

7. A housing for the tip of a disposable insertion endoscope, said housing comprising:
    a circumferential side wall having a first end, a second end, and a front wall arranged at the first end of said circumferential side wall, the first end being distal of the second end, and the circumferential wall and the front wall providing an internal compartment in said housing,
    said front wall comprising at least one transparent part made of a polymer material and adapted to protect a camera arranged in said internal compartment proximally of said at least one transparent part,
    said at least one transparent part comprising a first surface facing the internal compartment and a second surface opposite the first surface,
    wherein said second surface comprises at least one area having a nano-structure molded or stamped directly in said front wall,
    wherein the nano-structure in said at least one area comprises a predetermined pattern of features, the features comprising first features and second features,
    wherein a spacing between the first features is greater than a spacing between the second features,
    wherein the second features are disposed between adjacent ones of the first features, and
    wherein the first features are sized and structured to repel liquids and the second features are sized and structured to provide anti-reflective properties.

8. The housing of claim 7, wherein the features comprise protrusions extending from and perpendicular to a plane traversing the front wall.

9. The housing of claim 7, wherein the features are comprised of said polymer material.

10. The housing of claim 7, wherein the spacing between the first features is in the range of 200 nm to 300 nm.

11. The housing of claim 7, wherein the first features comprise protrusions having peaks with the spacing from one peak to a closest adjacent peak of the first features being less than 380 nm.

12. The housing of claim 4, wherein a remainder of the front wall surrounding the at least one area comprises a nano-structure comprising protrusions having peaks with a spacing from one peak to the closest adjacent peak in the range of 50 nm to 30 μm.

* * * * *